United States Patent
Tornier et al.

(10) Patent No.: US 7,470,287 B2
(45) Date of Patent: *Dec. 30, 2008

(54) SHOULDER OR HIP PROSTHESIS

(75) Inventors: Alain Tornier, Saint Ismier (FR); Thierry Manceau, Saint Martin D'heres (FR)

(73) Assignee: Tornier SAS, Saint Ismier (FR)

( * ) Notice: Subject to any disclaimer, the term of this patent is extended or adjusted under 35 U.S.C. 154(b) by 323 days.

This patent is subject to a terminal disclaimer.

(21) Appl. No.: 11/165,287

(22) Filed: Jun. 24, 2005

(65) Prior Publication Data

US 2005/0288791 A1 Dec. 29, 2005

(30) Foreign Application Priority Data

Jun. 28, 2004 (FR) ................................... 04 07071

(51) Int. Cl.
*A61F 2/40* (2006.01)

(52) U.S. Cl. ............... 623/19.13; 623/19.11; 623/19.12

(58) Field of Classification Search ... 623/19.11–19.14, 623/22.18, 22.43, 22.46, 20.14
See application file for complete search history.

(56) References Cited

U.S. PATENT DOCUMENTS

| | | | |
|---|---|---|---|
| 3,694,820 A | 10/1972 | Scales et al. | |
| 3,815,157 A | 6/1974 | Skorecki et al. | |
| 3,842,442 A | 10/1974 | Kolbel | |
| 3,864,758 A | 2/1975 | Skobel | |
| 3,869,730 A | 3/1975 | Skobel | |
| 3,916,451 A | 11/1975 | Buechel et al. | |
| 3,978,528 A | 9/1976 | Crep | |
| 3,979,778 A | 9/1976 | Stroot | |
| 3,992,726 A | 11/1976 | Freeman et al. | |

(Continued)

FOREIGN PATENT DOCUMENTS

DE 19509037 9/1996

(Continued)

OTHER PUBLICATIONS

Rochetin, U.S. Appl. No. 11/194,452, entitled "Patellar Retractor and Method of Surgical Procedure on Knee," filed Aug. 2, 2005.

(Continued)

*Primary Examiner*—Bruce E Snow
*Assistant Examiner*—Megan Wolf
(74) *Attorney, Agent, or Firm*—Faegre & Benson LLP (57) ABSTRACT

The prosthesis according to the invention comprises a first component, humeral or femoral, presenting a concave surface of articulation and a second, intermediate component presenting first and second convex surfaces of articulation intended to cooperate respectively with the concave surface of articulation of the first component and with a glenoidal or acetabular concave surface of articulation. The second component is hollow and defines a volume for receiving a head of a member belonging to the first component, this member being connected to a metaphyseal part of the first component by a stem, the head being connected to the second component by traversing an opening made in a ring of the second component mounted on a cup of which the outer surface forms the second convex surface of articulation of the second component. The first convex surface of articulation of the second component is formed on the outer surface of the ring, around the aforementioned opening.

26 Claims, 8 Drawing Sheets

U.S. PATENT DOCUMENTS

| | | | |
|---|---|---|---|
| 4,003,095 A | 1/1977 | Gristina | |
| 4,030,143 A | 6/1977 | Elloy et al. | |
| 4,040,131 A | 8/1977 | Gristina | |
| 4,054,955 A | 10/1977 | Seppo | |
| 4,135,517 A | 1/1979 | Reale | |
| 4,179,758 A * | 12/1979 | Gristina | 623/23.4 |
| 4,206,517 A | 6/1980 | Pappas et al. | |
| 4,261,062 A | 4/1981 | Amstutz et al. | |
| 4,550,450 A | 11/1985 | Kinnett | |
| 4,693,372 A | 9/1987 | Gabard | |
| 4,822,370 A | 4/1989 | Schelhas | |
| 4,846,840 A | 7/1989 | Leclercq et al. | |
| 4,865,605 A | 9/1989 | Dines et al. | |
| 4,865,609 A | 9/1989 | Roche | |
| 4,892,549 A | 1/1990 | Figgie, III et al. | |
| 4,919,670 A | 4/1990 | Dale et al. | |
| 4,957,510 A | 9/1990 | Cremascoli | |
| 4,963,155 A | 10/1990 | Lazzeri et al. | |
| 5,032,132 A | 7/1991 | Matsen, III et al. | |
| 5,080,673 A | 1/1992 | Burkhead et al. | |
| 5,080,685 A | 1/1992 | Bolesky et al. | |
| 5,127,920 A | 7/1992 | MacArthur | |
| 5,135,529 A | 8/1992 | Paxson et al. | |
| 5,163,961 A | 11/1992 | Harwin | |
| 5,171,289 A | 12/1992 | Tornier | |
| 5,181,928 A | 1/1993 | Bolesky et al. | |
| 5,192,329 A | 3/1993 | Christie et al. | |
| 5,201,882 A | 4/1993 | Paxson | |
| 5,206,925 A | 4/1993 | Nakazawa et al. | |
| 5,222,984 A | 6/1993 | Forte | |
| 5,261,914 A | 11/1993 | Warren | |
| 5,314,479 A | 5/1994 | Rockwood, Jr. et al. | |
| 5,314,485 A | 5/1994 | Judet | |
| 5,314,487 A | 5/1994 | Schryver et al. | |
| 5,326,359 A | 7/1994 | Oudard | |
| 5,330,531 A | 7/1994 | Capanna | |
| 5,358,526 A | 10/1994 | Tornier | |
| 5,383,936 A | 1/1995 | Kubein-Meesenburg et al. | |
| 5,405,399 A | 4/1995 | Tornier | |
| 5,425,779 A | 6/1995 | Schlosser | |
| 5,429,639 A | 7/1995 | Judet | |
| 5,443,519 A | 8/1995 | Averill et al. | |
| 5,458,650 A | 10/1995 | Carret et al. | |
| 5,462,563 A | 10/1995 | Shearer et al. | |
| 5,505,731 A | 4/1996 | Tornier | |
| 5,507,817 A | 4/1996 | Craig et al. | |
| 5,507,818 A | 4/1996 | McLaughlin | |
| 5,507,824 A | 4/1996 | Lennox | |
| 5,549,682 A | 8/1996 | Roy | |
| 5,580,352 A | 12/1996 | Sekel | |
| 5,591,168 A | 1/1997 | Judet et al. | |
| 5,662,651 A | 9/1997 | Tornier et al. | |
| 5,676,702 A | 10/1997 | Ratron | |
| 5,702,447 A | 12/1997 | Walch et al. | |
| 5,702,457 A | 12/1997 | Walch et al. | |
| 5,702,478 A | 12/1997 | Tornier | |
| 5,702,486 A | 12/1997 | Craig et al. | |
| 5,723,018 A | 3/1998 | Cyprien et al. | |
| 5,728,161 A | 3/1998 | Camino et al. | |
| 5,741,335 A | 4/1998 | Gerber et al. | |
| 5,755,807 A | 5/1998 | Anstaett et al. | |
| 5,766,256 A | 6/1998 | Oudard et al. | |
| 5,800,551 A | 9/1998 | Williamson et al. | |
| 5,824,106 A | 10/1998 | Fournol | |
| 5,879,395 A | 3/1999 | Tornier et al. | |
| 5,879,405 A | 3/1999 | Ries et al. | |
| 5,902,340 A | 5/1999 | White et al. | |
| 5,910,171 A | 6/1999 | Kummer et al. | |
| 5,928,285 A | 7/1999 | Bigliani | |
| 5,944,758 A | 8/1999 | Mansat et al. | |
| 5,961,555 A | 10/1999 | Huebner | |
| 5,984,927 A | 11/1999 | Wenstrom, Jr. et al. | |
| 6,015,437 A | 1/2000 | Stossel | |
| 6,033,439 A | 3/2000 | Camino et al. | |
| 6,045,582 A | 4/2000 | Prybyla | |
| 6,045,583 A | 4/2000 | Gross et al. | |
| 6,102,953 A | 8/2000 | Huebner | |
| 6,129,764 A | 10/2000 | Servfidio | |
| 6,162,254 A | 12/2000 | Timoteo | |
| 6,165,224 A | 12/2000 | Tornier | |
| 6,168,629 B1 | 1/2001 | Timoteo | |
| 6,171,341 B1 | 1/2001 | Boileau et al. | |
| 6,183,519 B1 | 2/2001 | Bonnin et al. | |
| 6,197,062 B1 | 3/2001 | Fenlin | |
| 6,197,063 B1 | 3/2001 | Dews | |
| 6,203,575 B1 | 3/2001 | Farey | |
| 6,206,925 B1 | 3/2001 | Tornier | |
| 6,228,120 B1 | 5/2001 | Leonard et al. | |
| 6,267,767 B1 | 7/2001 | Strobel et al. | |
| 6,283,999 B1 | 9/2001 | Rockwood, Jr. | |
| 6,299,646 B1 | 10/2001 | Chambat et al. | |
| 6,312,467 B1 | 11/2001 | McGee | |
| 6,328,758 B1 | 12/2001 | Tornier et al. | |
| 6,334,874 B1 | 1/2002 | Tornier et al. | |
| 6,364,910 B1 | 4/2002 | Shultz et al. | |
| 6,368,352 B1 | 4/2002 | Camino et al. | |
| 6,368,353 B1 | 4/2002 | Arcand | |
| 6,379,387 B1 | 4/2002 | Tornier | |
| 6,398,812 B1 | 6/2002 | Masini | |
| 6,406,495 B1 | 6/2002 | Schoch | |
| 6,406,496 B1 | 6/2002 | Rüter | |
| 6,436,144 B1 | 8/2002 | Ahrens | |
| 6,436,147 B1 | 8/2002 | Zweymuller | |
| 6,454,809 B1 | 9/2002 | Tornier | |
| 6,458,136 B1 | 10/2002 | Allard et al. | |
| 6,475,243 B1 | 11/2002 | Sheldon et al. | |
| 6,488,712 B1 | 12/2002 | Tornier et al. | |
| 6,494,913 B1 | 12/2002 | Huebner | |
| 6,506,214 B1 | 1/2003 | Gross | |
| 6,508,840 B1 | 1/2003 | Rockwood, Jr. et al. | |
| 6,514,287 B2 | 2/2003 | Ondrla et al. | |
| 6,520,994 B2 | 2/2003 | Nogarin | |
| 6,530,957 B1 | 3/2003 | Jack | |
| 6,540,770 B1 | 4/2003 | Tornier et al. | |
| 6,558,425 B2 | 5/2003 | Rockwood | |
| 6,569,202 B2 | 5/2003 | Whiteside | |
| 6,582,469 B1 | 6/2003 | Tornier | |
| 6,589,281 B2 | 7/2003 | Hyde, Jr. | |
| 6,599,295 B1 | 7/2003 | Tornier et al. | |
| 6,620,197 B2 | 9/2003 | Maroney et al. | |
| 6,626,946 B1 | 9/2003 | Walch et al. | |
| 6,673,114 B2 | 1/2004 | Hartdegen et al. | |
| 6,673,115 B2 | 1/2004 | Resch et al. | |
| 6,679,916 B1 | 1/2004 | Frankle et al. | |
| 6,736,851 B2 | 5/2004 | Maroney et al. | |
| 6,746,487 B2 | 6/2004 | Scifert et al. | |
| 6,749,637 B1 | 6/2004 | Bahler | |
| 6,755,866 B2 | 6/2004 | Southworth | |
| 6,761,740 B2 | 7/2004 | Tornier | |
| 6,767,368 B2 | 7/2004 | Tornier | |
| 6,780,190 B2 | 8/2004 | Maroney | |
| 6,783,549 B1 | 8/2004 | Stone et al. | |
| 6,790,234 B1 | 9/2004 | Frankle | |
| 6,802,864 B2 | 10/2004 | Tornier | |
| 6,824,567 B2 | 11/2004 | Tornier et al. | |
| 6,863,690 B2 | 3/2005 | Ball et al. | |
| 6,875,234 B2 | 4/2005 | Lipman et al. | |
| 6,887,277 B2 | 5/2005 | Rauscher et al. | |
| 6,890,357 B2 | 5/2005 | Tornier | |
| 6,890,358 B2 | 5/2005 | Ball et al. | |
| 6,942,699 B2 | 9/2005 | Stone et al. | |
| 6,953,478 B2 | 10/2005 | Bouttens et al. | |
| 6,969,406 B2 | 11/2005 | Tornier | |
| 7,011,686 B2 | 3/2006 | Ball et al. | |

| | | | |
|---|---|---|---|
| 7,033,396 B2 * | 4/2006 | Tornier .................... 623/19.11 |
| 7,066,959 B2 | 6/2006 | Errico |
| 7,108,719 B2 | 9/2006 | Horber |
| 7,166,132 B2 | 1/2007 | Callaway et al. |
| 7,169,184 B2 | 1/2007 | Dalla Pria |
| 7,175,663 B1 | 2/2007 | Stone |
| 7,195,645 B2 | 3/2007 | Disilvestro et al. |
| 7,238,207 B2 | 7/2007 | Blatter et al. |
| 7,238,208 B2 | 7/2007 | Camino et al. |
| 7,297,163 B2 | 11/2007 | Huebner |
| 7,309,360 B2 | 12/2007 | Tornier et al. |
| 7,329,284 B2 | 2/2008 | Maroney et al. |
| 7,338,498 B2 | 3/2008 | Long et al. |
| 7,338,528 B2 | 3/2008 | Stone et al. |
| 2001/0032021 A1 | 10/2001 | McKinnon |
| 2001/0047210 A1 | 11/2001 | Wolf |
| 2001/0049561 A1 | 12/2001 | Dews et al. |
| 2002/0032484 A1 | 3/2002 | Hyde, Jr. |
| 2002/0099381 A1 | 7/2002 | Maroney |
| 2002/0138148 A1 | 9/2002 | Hyde, Jr. |
| 2002/0143402 A1 | 10/2002 | Steinberg |
| 2002/0151982 A1 | 10/2002 | Masini |
| 2003/0009170 A1 | 1/2003 | Tornier |
| 2003/0009171 A1 | 1/2003 | Tornier |
| 2003/0028198 A1 | 2/2003 | Tornier et al. |
| 2003/0074072 A1 * | 4/2003 | Errico et al. ............. 623/17.14 |
| 2003/0097183 A1 | 5/2003 | Rauscher et al. |
| 2003/0114933 A1 | 6/2003 | Bouttens et al. |
| 2003/0149485 A1 | 8/2003 | Tornier |
| 2003/0158605 A1 | 8/2003 | Tornier |
| 2004/0002765 A1 | 1/2004 | Maroney et al. |
| 2004/0006392 A1 | 1/2004 | Grusin et al. |
| 2004/0030394 A1 | 2/2004 | Horber |
| 2004/0034431 A1 | 2/2004 | Maroney et al. |
| 2004/0039449 A1 * | 2/2004 | Tornier .................... 623/19.13 |
| 2004/0064189 A1 | 4/2004 | Maroney et al. |
| 2004/0064190 A1 | 4/2004 | Ball et al. |
| 2004/0133276 A1 | 7/2004 | Lang et al. |
| 2004/0134821 A1 | 7/2004 | Tornier |
| 2004/0138754 A1 | 7/2004 | Lang et al. |
| 2004/0148033 A1 | 7/2004 | Schroeder |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0210220 A1 | 10/2004 | Tornier |
| 2004/0210317 A1 | 10/2004 | Maroney et al. |
| 2004/0215200 A1 | 10/2004 | Tornier et al. |
| 2004/0220673 A1 | 11/2004 | Pria |
| 2004/0220674 A1 | 11/2004 | Pria |
| 2004/0225367 A1 | 11/2004 | Glien et al. |
| 2004/0230197 A1 | 11/2004 | Tornier et al. |
| 2004/0267370 A1 | 12/2004 | Ondria |
| 2005/0008672 A1 | 1/2005 | Winterbottom et al. |
| 2005/0015154 A1 | 1/2005 | Lindsey et al. |
| 2005/0043805 A1 | 2/2005 | Chudik |
| 2005/0049709 A1 | 3/2005 | Tornier |
| 2005/0055102 A1 | 3/2005 | Tornier et al. |
| 2005/0065612 A1 | 3/2005 | Winslow |
| 2005/0085919 A1 | 4/2005 | Durand-Allen et al. |
| 2005/0085921 A1 | 4/2005 | Gupta et al. |
| 2005/0090902 A1 | 4/2005 | Masini |
| 2005/0107882 A1 | 5/2005 | Stone et al. |
| 2005/0113931 A1 | 5/2005 | Horber |
| 2005/0119531 A1 | 6/2005 | Sharratt |
| 2005/0143829 A1 | 6/2005 | Ondria et al. |
| 2005/0165490 A1 | 7/2005 | Tornier |
| 2005/0177241 A1 | 8/2005 | Angibaud et al. |
| 2005/0197708 A1 | 9/2005 | Stone et al. |
| 2005/0203536 A1 | 9/2005 | Laffargue et al. |
| 2005/0209700 A1 | 9/2005 | Rockwood et al. |
| 2005/0216092 A1 | 9/2005 | Marik et al. |
| 2005/0251263 A1 | 11/2005 | Forrer et al. |
| 2005/0256684 A1 | 11/2005 | Farrar |
| 2005/0267590 A1 | 12/2005 | Lee |
| 2005/0278030 A1 | 12/2005 | Tornier et al. |
| 2005/0278031 A1 | 12/2005 | Tornier et al. |
| 2005/0278032 A1 | 12/2005 | Tornier et al. |
| 2005/0278033 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0009852 A1 | 1/2006 | Winslow et al. |
| 2006/0015185 A1 | 1/2006 | Chambat et al. |
| 2006/0020344 A1 | 1/2006 | Schultz et al. |
| 2006/0030946 A1 | 2/2006 | Ball et al. |
| 2006/0173457 A1 | 8/2006 | Tornier |
| 2006/0235538 A1 | 10/2006 | Rochetin et al. |
| 2006/0241775 A1 | 10/2006 | Buss |
| 2007/0225817 A1 | 9/2007 | Reubelt et al. |
| 2007/0225818 A1 | 9/2007 | Reubelt et al. |
| 2007/0225821 A1 | 9/2007 | Reubelt et al. |
| 2007/0244564 A1 | 10/2007 | Ferrand et al. |
| 2007/0250174 A1 | 10/2007 | Tornier et al. |

FOREIGN PATENT DOCUMENTS

| | | |
|---|---|---|
| DE | 19630298 | 1/1998 |
| EP | 0257359 | 8/1987 |
| EP | 0299889 | 1/1989 |
| EP | 0524857 | 1/1993 |
| EP | 0549480 | 6/1993 |
| EP | 0599429 | 6/1994 |
| EP | 0617934 | 10/1994 |
| EP | 0664108 | 7/1995 |
| EP | 0679375 | 11/1995 |
| EP | 0712617 | 5/1996 |
| EP | 0715836 | 6/1996 |
| EP | 0797964 | 10/1997 |
| EP | 0807426 | 11/1997 |
| EP | 0809986 | 12/1997 |
| EP | 0864306 | 9/1998 |
| EP | 0903127 | 3/1999 |
| EP | 0903128 | 3/1999 |
| EP | 0927548 | 7/1999 |
| EP | 1062923 | 12/2000 |
| EP | 1064890 | 1/2001 |
| EP | 1195149 | 10/2002 |
| EP | 1380274 | 1/2004 |
| EP | 1402854 | 3/2004 |
| FR | 2248820 | 5/1975 |
| FR | 2545352 | 11/1984 |
| FR | 2574283 | 6/1986 |
| FR | 2652498 | 4/1991 |
| FR | 2664809 | 1/1992 |
| FR | 2699400 | 6/1994 |
| FR | 2721200 | 12/1995 |
| FR | 2726994 | 5/1996 |
| FR | 2737107 | 1/1997 |
| FR | 2835425 | 8/2003 |
| FR | 2836039 | 8/2003 |
| SU | 749392 | 7/1980 |
| WO | WO 91/07932 | 6/1991 |
| WO | WO 9107932 | 6/1991 |
| WO | WO 93/09733 | 5/1993 |
| WO | WO 9309733 | 5/1993 |
| WO | WO 96/17553 | 6/1996 |
| WO | WO 9617553 | 6/1996 |
| WO | WO 98/46172 | 10/1998 |
| WO | WO 9846172 | 10/1998 |
| WO | WO 9949792 | 10/1999 |
| WO | WO 9965413 | 12/1999 |
| WO | WO 0015154 | 3/2000 |
| WO | WO 0041653 | 7/2000 |
| WO | WO 0147442 | 7/2001 |
| WO | WO 0239931 | 5/2002 |
| WO | WO 0239933 | 5/2002 |

| | | |
|---|---|---|
| WO | WO 02067821 | 9/2002 |
| WO | WO 03005933 | 1/2003 |
| WO | WO03/094806 | 11/2003 |
| WO | WO2007/109319 | 2/2007 |
| WO | WO2007/109291 | 9/2007 |
| WO | WO2007/109340 | 9/2007 |

OTHER PUBLICATIONS

Rochetin et al., U.S. Appl. No. 11/401,415, entitled "Surgical Apparatus for Implantation of a Partial or Total," filed Apr. 11, 2006.
Rochetin, U.S. Appl. No. 11/670,274, entitled "Offset Stern Tibial Implantation," filed Feb. 1, 2007.
Ratron et al., U.S. Appl. No. 11/626,735, entitled "Surgical Instrumentation Kit for Inserting Ankle Prosthesis," filed Jan. 24, 2007.
John M. Fenlin Jr., M.D., Symposium on Surgery of the Shoulder, "Total Glenohumeral Joint Replacement," *Othopedic Clinics of North America*, vol. 6, No. 2, Apr. 1975, pp. 565-583.
"Aequalis-Fracture Suture Technique in 5 Steps," Tornier, Inc.
"Aequalis-Fracture Shoulder Prosthesis—Surgical Technique," Tornier, Inc.
"Aequalis® Press-Fit Shoulder Prosthesis—Surgical Technique," Tornier, Inc.
"Anatomical Shoulder™—Cemented Shoulder Prosthesis Product Information and Surgical Technique," Sulzer Medica, 2000.
"Anatomical Shoulder™ System Surgical Technique—Removable head option for improved surgical results," Zimmer, Inc., 2004.
Bigliani/Flatow®—The Complete Shoulder Solution, 4-Part Fracture of the Humerus Surgical Technique, Zimmer, Inc., 2000.
"Bio-Modular®/ Bi-Polar Shoulder Arthroplasty," Biomet, Inc., 1997.
"Bio-Modular® Choice, Shoulder System," Biomet Orthopedics, Inc., 2004.
"Bio-Modular Total Shoulder Surgical Technique," Biomet Orthopedics, Inc., 2001.
"Copeland™ Humeral Resurfacing Head," Biomet Orthopedics, Inc., 2001.
"Global C.A.P.™ Surgical technique, resurfacing humeral head implant," DePuy International, Ltd., 2004.
Boileau, et al. "Adaptability and modularity of shoulder prosthese," *Maitrise Orthopédique*, https://www.maitriseorthop.com/corpusmaitri/orthopaedic/prothese_epaule_orthop/boileau_us.shtml, Jan. 3, 2006.
Boileau, et al. "Arthroscopic Repair of Full-Thickness Tears of the Supraspinatus: Does the tendon really heal?," *The Journal of Bone and Joint Surgery, Inc.*, pp. 1229-1240, 2005.
"Design Rationale," Latitude®.

Klein, Travis J., et al. "Mechanically favorable bone remodeling in rotator cuff arthropathy patients with good function," *Minneapolis Sports Medicine Center and University of Minnesota*.
Mansat, Michel, "Neer 3™, Surgical Technique for Fractrures," Smith & Nephew, 2000.
Molé, M.D., et al., "Aequalis-Reversed™ Shoulder Prosthesis, Surgical Technique," Tornier, Inc.
Nicholson, Gregory P., "Arthroplasty and Rotator Cuff Deficiency," Chapter 7, pp. 149-166.
"Offset Head, Bio-Modular® Total Shoulder," Biomet, Inc. 2000.
"The Foundation® Total Shoulder System," Encore Surgical.
"The Townley Modular Shoulder, Design by Reason," Biopro, Inc.
Zimmer® Bigliani/Flatow®—The Complete Shoulder Solution, Total Shoulder Arthroplasty Surgical Technique, Zimmer, Inc., 2003.
"Zimmer® Shoulder Retractors, " Zimmer, Inc., 2000.
"Anatomic Glenoid, Surgical Technique," Smith & Nephew, 2000.
"Anatomical Shoulder® System—The new removable head option," Zimmer Inc., 2004.
"Delta CTA™ Reverse Shoulder Prosthesis," DePuy International, Ltd., 2004.
Cofield, M.D., Robert H. "Cofield[2] Total Shoulder System, Surgical Technique," Smith & Nephew, 1997.
"Aequalis®-Glenoid Keeled and Pegged—Surgical Technique," Tornier, Inc.
"Bigliani/Flatow®—The Complete Shoulder Solution, Designed by Shoulder Surgeons for Shoulder Surgery," Zimmer, Inc., 2001.
"Tornier Surgical Technique Addendum, Tornier Aequalis® Reversed Hemi-Adaptor Technique," Tornier, Inc., Aug. 8, 2005.
"Tornier Surgical Technique Addendum, Aequalis® Reversed Shoulder Polyethylene Insert," Tornier, Inc., Aug. 8, 2005.
Beuchel M.D., Frederick F. "Beuchel-Pappas™ Modular Salvage Shoulder System," Endotec, Inc., 2000.
Beuchel M.D., Frederick F. "Beuchel-Pappas™ Resurfacing Shoulder System," Endotec, Inc., 2000.
Beuchel M.D., Frederick F. "Beuchel-Pappas™ Total Shoulder System," Endotec, Inc., 2000.
Hertel M.D., PD, Ralph. "Technical considerations for implantation of EPOCA glenoid components (Leseprobe)," *Epoca Newsletter*, May 14, 2001.
Apoil, André "A Condyle for the Rotator Cuff Muscles, the total shoulder prosthesis," Aesculap®, 1994.
"Tornier Aequalis® Reversed 2 Prong Capsular Retractor," Tornier, Inc., Oct. 8, 2005.
"Tornier Aequalis® Reversed Shoulder G2 Baseplate," Tornier, Inc., Oct. 8, 2005.
Boileau et al., U.S. Appl. No. 12/020,913, entitled "Method and Apparatus for Fitting a Shoulder Prosthesis"filed Jan. 28, 2008.

* cited by examiner

SHOULDER OR HIP PROSTHESIS

FIELD OF THE INVENTION

The present invention relates to a total or partial shoulder or hip prosthesis enabling the characteristics of a natural joint to be reproduced with good precision.

BACKGROUND OF THE INVENTION

FR-A-2 841 768 discloses making a shoulder or hip prosthesis which comprises an intermediate element formed by a cup and a washer defining two convex surfaces intended to cooperate respectively with a concave surface of articulation formed by a plate connected to the humeral or femoral component and a natural or prosthetic, glenoidal or acetabular concave surface of articulation. The positioning of the plate between the intermediate component and the humeral or femoral component has the effect of inducing relatively large dimensions of the prosthesis in a direction parallel to the median axis of a stem connecting this plate to a part of the humeral or femoral component anchored in the corresponding bone. This results in an offset between the humerus and the glenoid cavity or between the femur and the pelvis, such an offset proving, for these pathologies, to give discomfort to the patient.

It is a more particular object of the invention to overcome these drawbacks by proposing a novel shoulder or hip prosthesis, thanks to which the 20 distance between the humeral or femoral plane of section, on the one hand, and the glenoidal or acetabular articular surface, on the other hand, may be reduced.

SUMMARY OF THE INVENTION

In this spirit, the invention relates to a shoulder or hip prosthesis comprising a first component, humeral or femoral, presenting a concave surface of articulation and a second, intermediate component presenting first and second convex surfaces of articulation intended to cooperate respectively with the concave surface of articulation of the first component and with a glenoidal or acetabular concave surface of articulation which is natural or defined by a third, glenoidal or acetabular component, this second component being hollow and defining a volume for receiving a head of a member belonging to the first component, this member being connected to a metaphyseal part of the first component by a stem. The head is connected to the second component by traversing an opening made in a ring belonging to this second component and mounted on a cup of which the outer surface forms the aforementioned second convex surface of articulation. This prosthesis is characterized in that the first convex surface of articulation of the second component is formed on the outer surface of the ring, around the aforementioned opening.

Thanks to the invention, the first convex surface of articulation of the second component is formed on the outside of the latter, this allowing it to interact with a surface of the first component adjacent its metaphyseal part, and even borne by the latter. This results in a good compactness of the prosthesis which is well adapted to certain pathologies.

According to advantageous but non-obligatory aspects, a shoulder or hip prosthesis may incorporate one or more of the following characteristics taken in any technically admissible combination:

The opening of the ring of the second component is elongated, with a width less than a maximum width of the part of the member received in the interior volume of the second component, the width of this opening being slightly greater than a width of the aforementioned stem. Thanks to this aspect of the invention, the head of the member of the first component is retained inside the volume of the second component, this ensuring good hold of the assembly, while the width of the opening allows a guiding in translation of the member of the first component at the level of its stem.

According to a first form of embodiment, the concave surface of articulation of the first component is formed on a portion of the aforementioned member which is in one piece with the head introduced in the interior volume of the second component and the associated stem, this member being added on a metaphyseal part of the first component. According to another embodiment, the concave surface of articulation of the first component is formed on a metaphyseal part of the first component.

Whatever the form of embodiment considered, one of the first convex surface of the second component and the concave surface of the first component may project with respect to the component to which it belongs, while the other of these surfaces is recessed with respect to the other component, the projecting surface being bordered by two globally parallel edges, while the recessed surface is bordered by two globally parallel edges between which the edges of the projecting surface are disposed when the prosthesis is in a mounted configuration.

One of the first and second components forms a hollow slideway for receiving and guiding a projecting part of the other component, from the first and second components, the first convex surface of articulation of the second component and the concave surface of articulation of the first component being respectively formed by a bottom of this slideway and by an end surface of the projecting part, or vice versa.

The opening of the ring is provided with a widened zone of introduction of the head of the member in the receiving volume of the second component. This ring may be elastically deformable at least at the level of the widened zone, so as to allow the introduction of the head in the volume. In another approach, the widened zone may be made at one end of the opening of the ring which is elongated, the first or the second component, and even the two, being provided with at least one element in relief for blocking, adapted to prevent the alignment of the head and this widened zone when the prosthesis is in a mounted configuration.

The first surface of articulation is globally in the form of a truncated cylinder centred on an antero-posterior axis of the joint when the prosthesis is in mounted and implanted configuration.

BRIEF DESCRIPTION OF THE DRAWINGS

The invention will be more readily understood and other advantages thereof will appear more clearly in the light of the following description of three forms of embodiment of a prosthesis in accordance with its principle, given solely by way of example and made with reference to the accompanying drawings, in which.

DESCRIPTION OF PREFERRED EMBODIMENTS

Referring now to the drawings and in order to render them clearer, the bones in which the prosthetic components are implanted have been shown solely in FIGS. 1 to 3, 5, 6 and 8.

The prosthesis P shown in FIGS. 1 to 4 comprises a humeral component 1 which includes a stem 11 intended to be anchored in the medullary canal of the patient's humerus H and of which the metaphyseal part 12 comprises a truncated housing 13 for receiving and wedging a shank 14 for anchoring a member or stud 15 intended to be added and immobilized on the stem 11. This member, which is in one piece, also comprises a neck 16 in the form of a stem which connects a globally spherical head 17 to the principal part of the member 15 which comprises the shank 14. The member 15 is also provided with a globally rectangular flange 18 of which the outer shape allows it to be engaged in a globally rectangular depression 19 made on the part 12, around the housing 13.

$S_1$ denotes the concave surface of the flange 18 turned towards the head 17. $X_1$ denotes the longitudinal axis of the elements 14 and 16. $Y_1$ denotes a longitudinal axis of the depression 19 parallel to its largest sides and located at equal distance therefrom. The surface $S_1$ is a portion of a cylinder with rectilinear generatrix and with circular base, centred on an axis $Z_1$ perpendicular to the axes $X_1$ and $Y_1$, axis $Z_1$ being located globally in an antero-posterior direction of the shoulder when the prosthesis is in mounted and implanted configuration.

The prosthesis P also comprises a glenoidal component 2 anchored in the glenoid cavity G and defining a concave surface $S_2$ whose concavity is turned towards the outside of the glenoid cavity.

Between the components 1 and 2 there is disposed an intermediate component 3 comprising a hollow cup 31 inside which is immobilized by any appropriate means a ring 32 which defines an elongated opening 33 of which the largest dimension extends along an axis $Y_3$ globally parallel to axis $Y_1$ when the prosthesis is in mounted configuration.

In its median part, the opening 33 is provided with a widened zone 34 through which the head 17 is intended to be introduced by force in a volume $V_3$ defined inside the component 3, between the cup 31 and the ring 32.

The ring 32 is made of plastics material, particularly polyethylene, which allows it to be elastically deformed at the level of the zone 34, when the head 17 is introduced in the volume $V_3$. In order to facilitate this introduction, the zone 34 is convergent in the direction of the volume $V_3$.

The diameter $d_{17}$ of the head 17 is greater than the width $l_{33}$ of the opening 33, including at the level of the zone 34, while the diameter $d_{16}$ of the neck 16 is slightly less than this width. In this way, when the head 17 has been introduced in the volume $V_3$, it resists an effort of separation of the elements 1 and 3 and contributes to the tear-away resistance of the prosthesis P. The respective values of the diameter $d_{16}$ and of the width $l_{33}$ are compatible with the translation of the neck or stem 16 in the longitudinal direction $Y_3$ of the opening 33.

$S'_2$ denotes the convex outer surface of the cup 31. $S'_1$ denotes the part of the outer surface 35 of the ring 32 which surrounds the opening 33. The surface 35 is the surface of the ring 32 facing opposite the volume $V_3$.

The surface $S'_2$ is a portion of sphere with a radius similar to that of the surface $S_2$, this allowing a surface articulation of the surfaces $S_2$ and $S'_2$ on each other.

The surface $S'_1$ is a portion of a cylinder with rectilinear generatrix and with circular base centred on an axis $Z_3$ perpendicular to axis $Y_3$ and merged with axis $Z_1$ when the surfaces $S_1$ and $S'_1$ are in abutment on each other.

In this way, the articulation of the humerus H with respect to the glenoid cavity G takes place by slide of the surfaces $S_1$ and $S'_1$ on each other and of surfaces $S_2$ and $S'_2$ on each other.

The surface $S'_1$ is hollowed with respect to the rest of the outer surface 35 of the ring 32 which forms a sort of slideway. The surface $S'_1$ is defined between the two edges 36 and 36' of this slideway, parallel to the axis $Y_3$ and separated by a distance $d_{36}$ slightly greater than the width $l_{18}$ of the flange 18. In this way, the flange 18 may be partially engaged between the edges 36 and 36', this contributing to the guiding in translation of the component 3 with respect to the component 1.

The inner surface 39 of the ring 32 has the same radius of curvature as the surface 35.

According to a variant of the invention (not shown), the surfaces $S_1$ and $S'_1$ may be portions of a sphere instead of portions of a cylinder. In that case, the guiding of the stem 16 in translation is essentially ensured by the edges of the slideway.

According to a variant of the invention (not shown), the axis $Y_1$-$Y'_1$ of the depression 19 may be located in an antero-posterior direction, while axis $Z_1$ is located in a supero-inferior direction. Such a variant promotes the movement of abduction.

According to other variants (not shown), the head 17 may take different shapes, for example frustum of cone.

Figure 1:
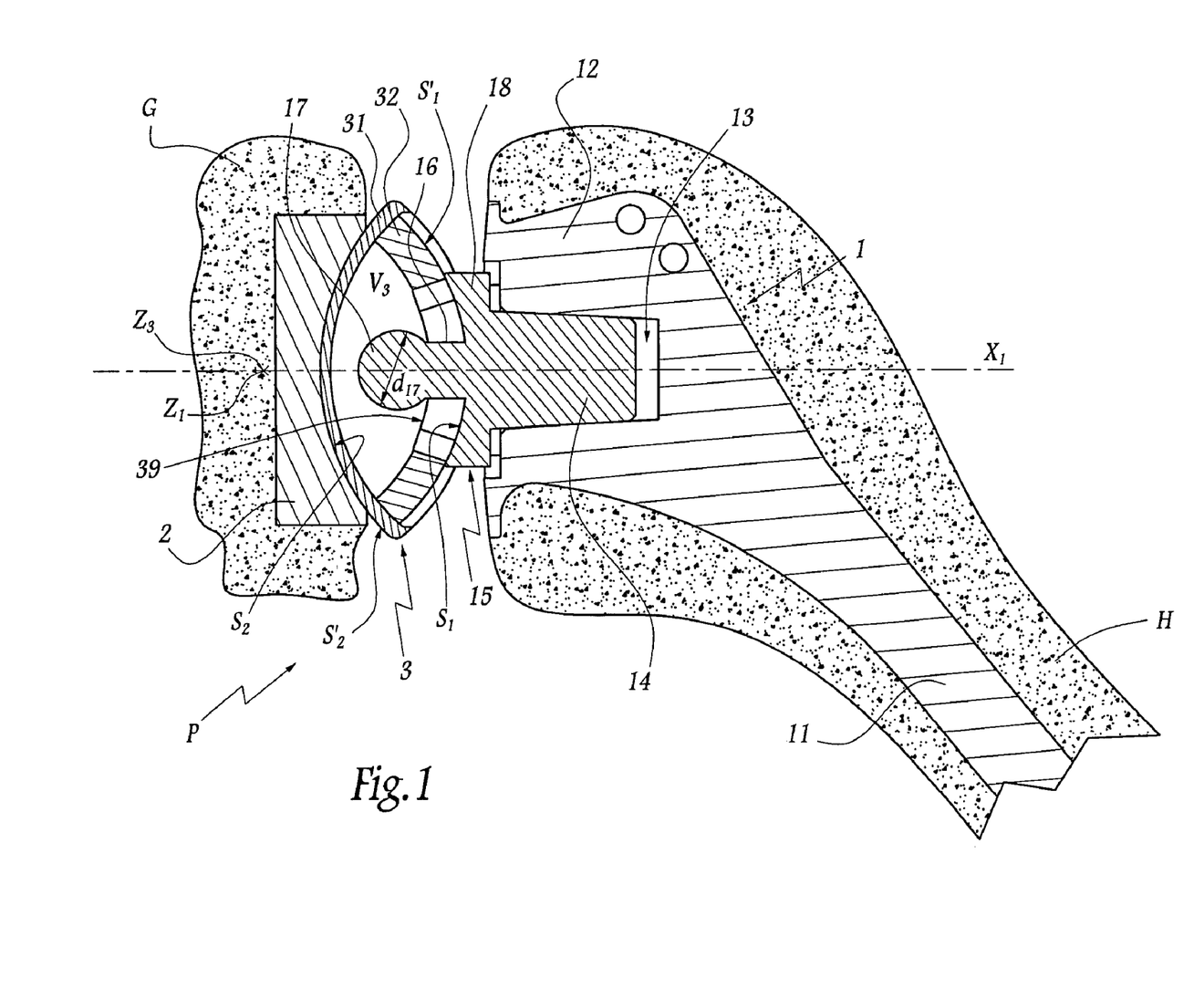
FIG. 1 is a sagittal section of a shoulder prosthesis according to the invention in place on a patient, while the patient's arm is in intermediate position.
Figure 2:
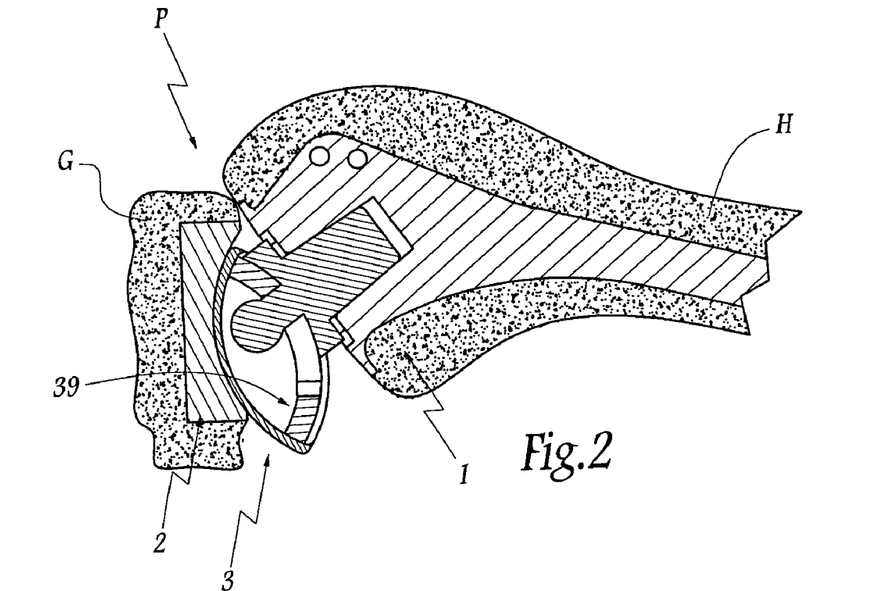
FIG. 2 is a section similar to FIG. 1 on a smaller scale, while the patient's arm is in raised position with respect to that of FIG. 1.
Figure 3:
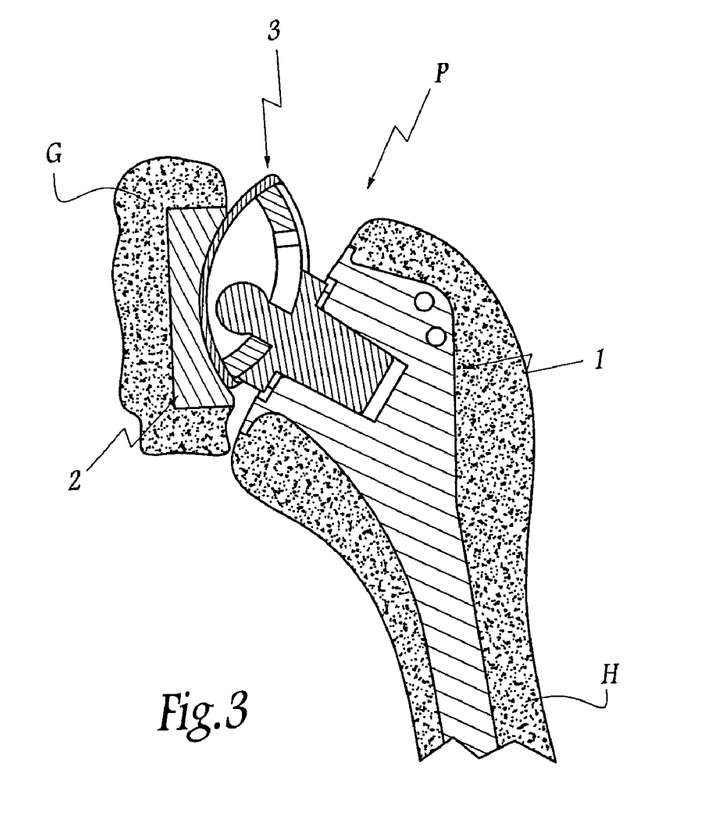
FIG. 3 is a section similar to FIG. 2, while the patient's arm is in low position.
Figure 4:
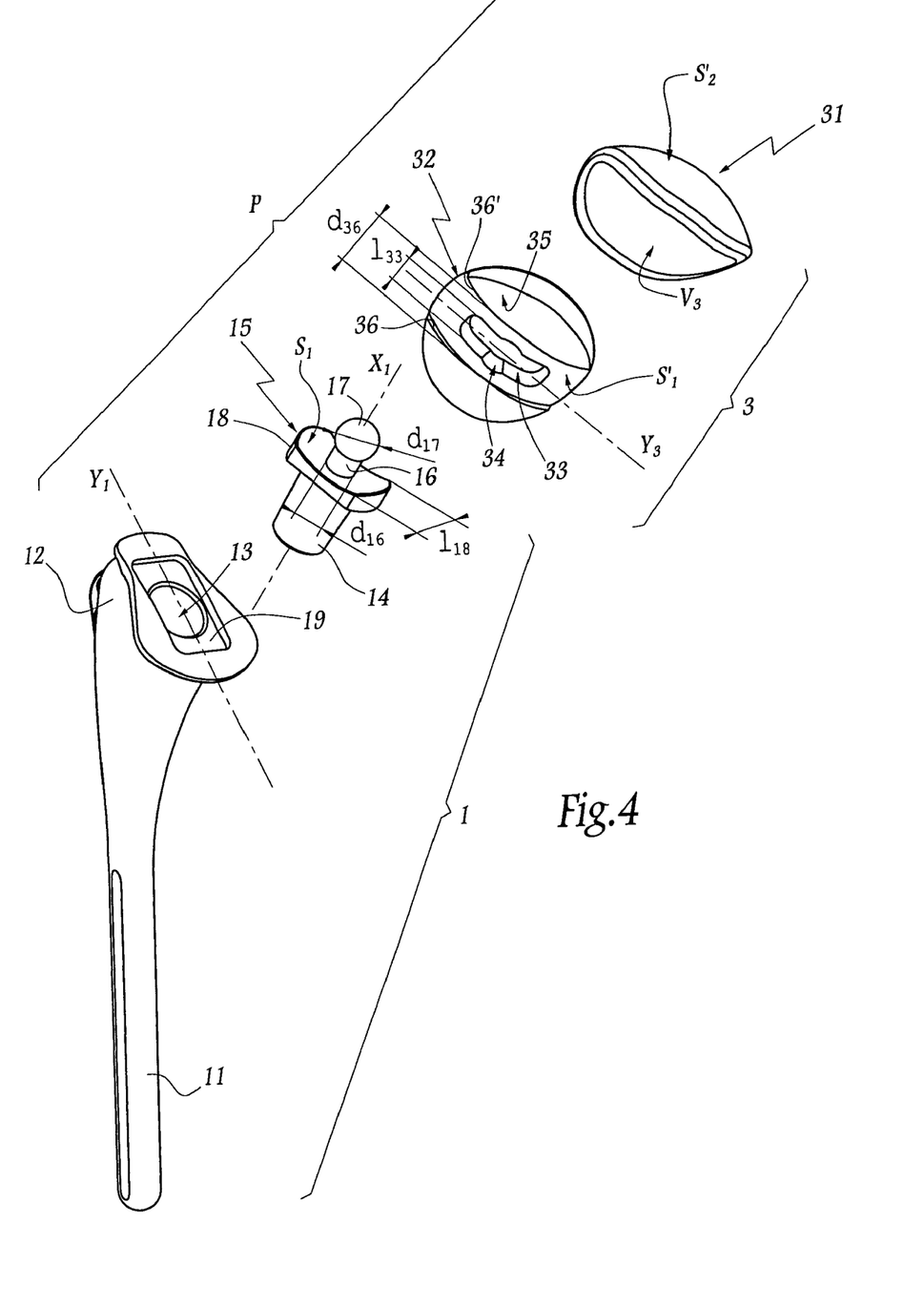
FIG. 4 is an exploded view in perspective of the humeral and intermediate components of the prosthesis of FIGS. 1 to 3.
Figure 5:
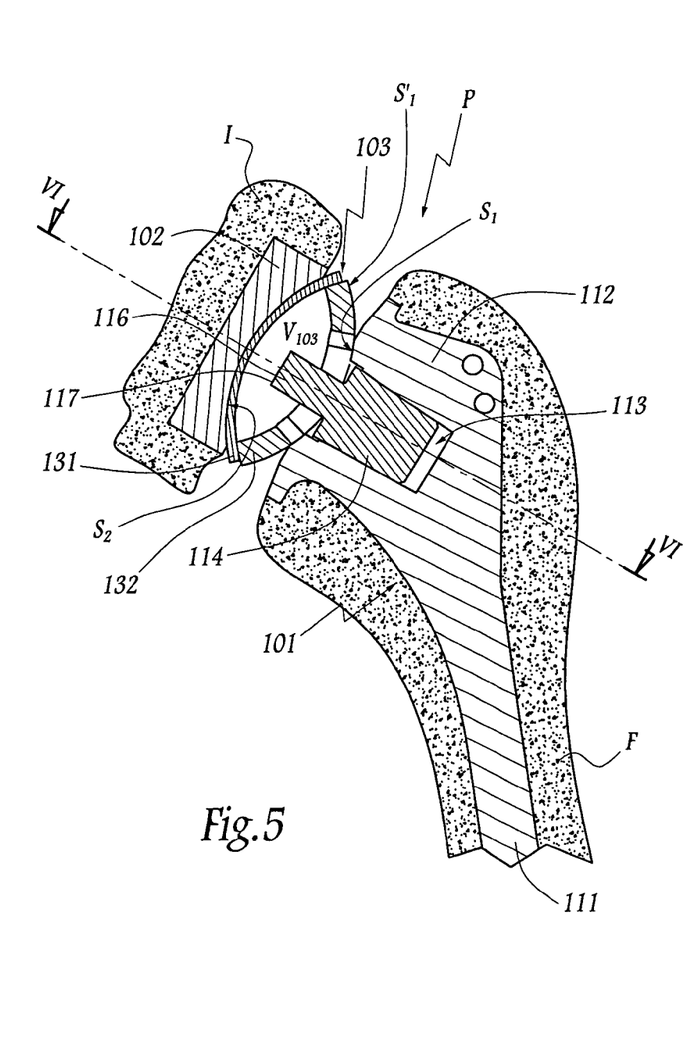
FIG. 5 is a section similar to FIG. 1 for a hip prosthesis in accordance with a second form of embodiment of the invention.
Figure 6:
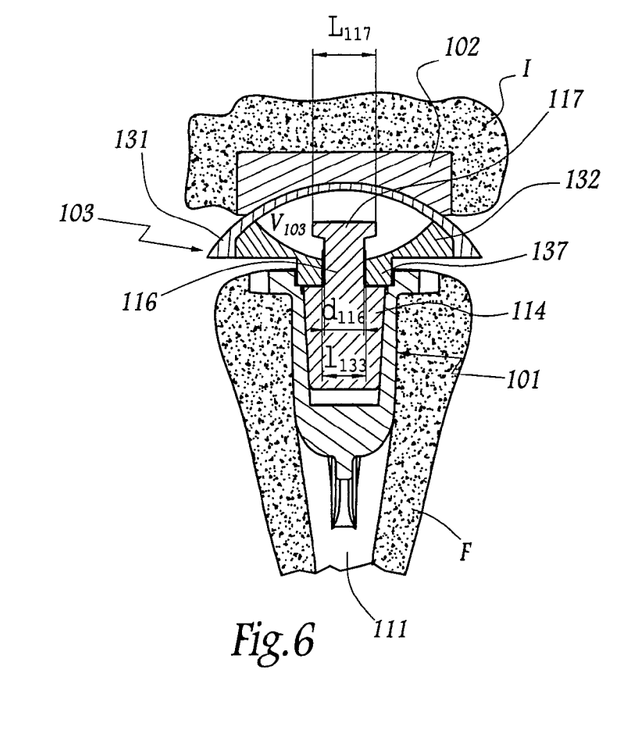
FIG. 6 is a section along line VI-VI in FIG. 5.
Figure 7:
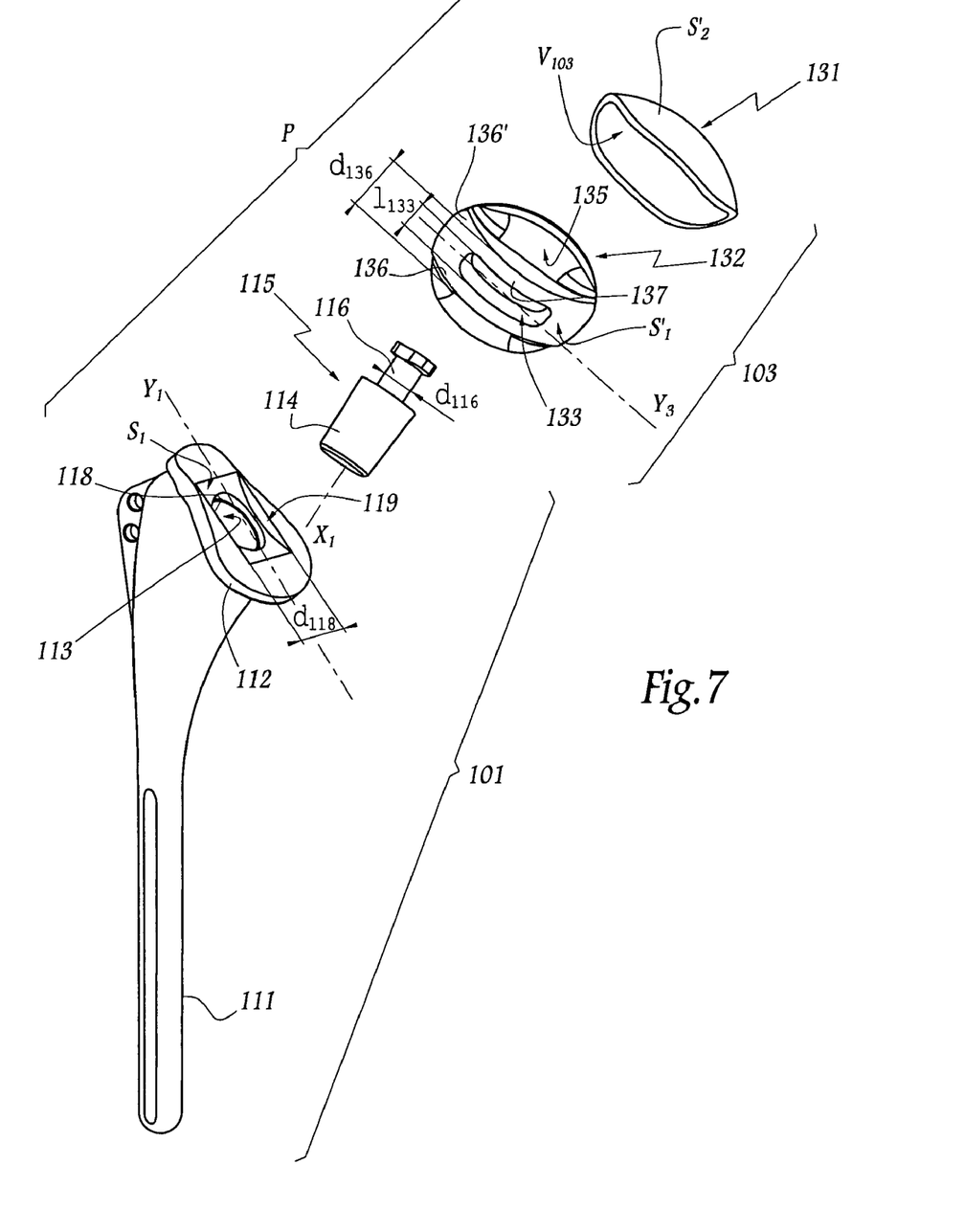
FIG. 7 is an exploded view in perspective of the femoral and intermediate components of the prosthesis of FIGS. 5 and 6.
Figure 8:
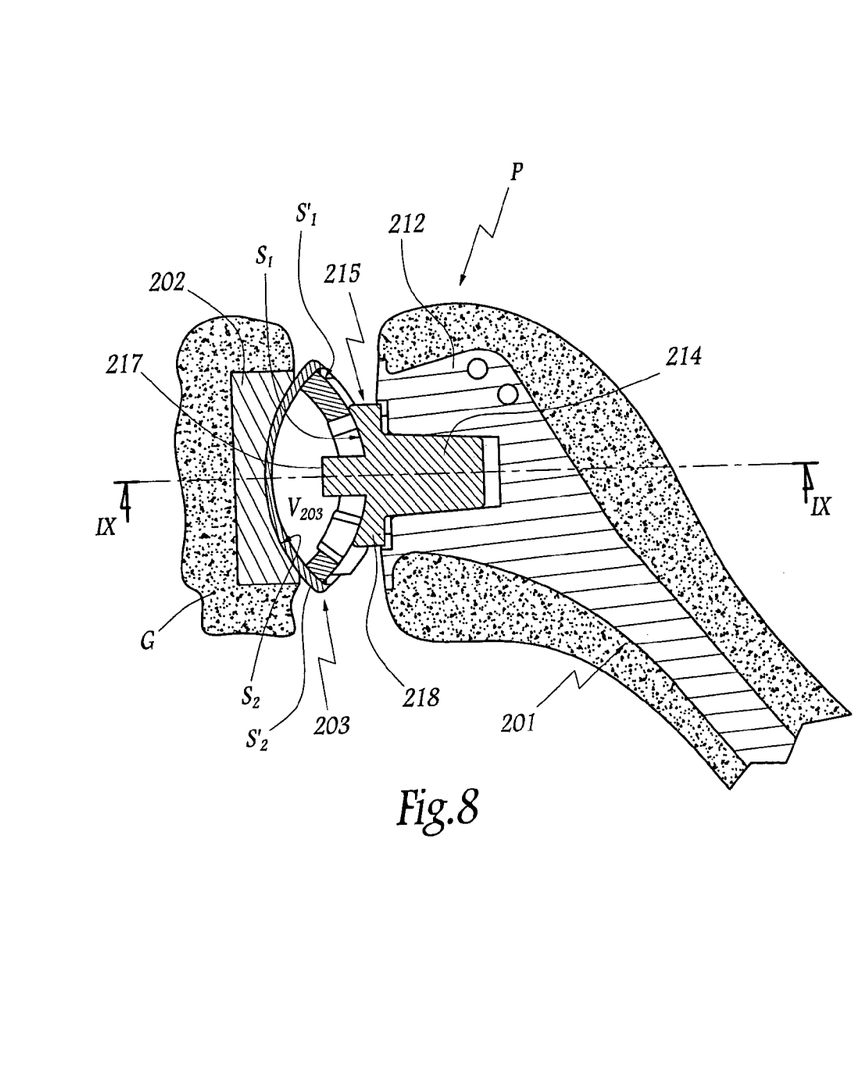
FIG. 8 is a section similar to FIG. 1 for a shoulder prosthesis in accordance with a third form of embodiment according to the invention.
Figure 9:
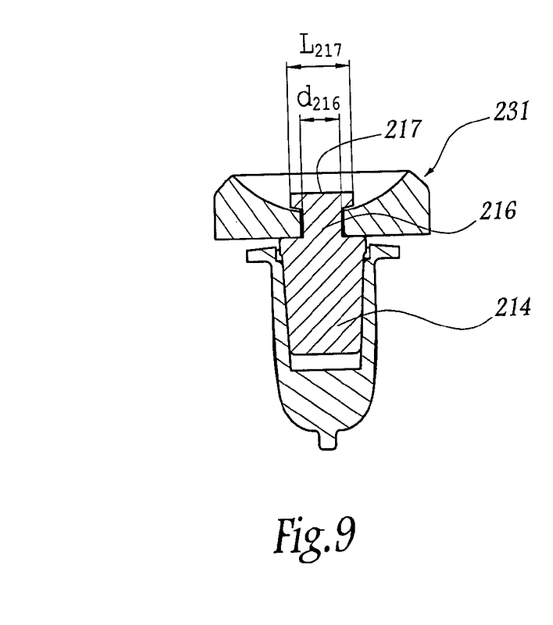
FIG. 9 is a section along line IX-IX in FIG. 8.

In the second form of embodiment of the invention shown in FIGS. 5 to 7, elements similar to those of the first embodiment bear identical references increased by 100. The prosthesis P of this embodiment is intended to fit a patient's hip. A femoral component 101 comprises a stem 111 intended to be anchored in the medullary canal of the femur F, and a metaphyseal part 112 in which is made a housing 113 for receiving and blocking a shank 114 for anchoring a one-piece member 115 which comprises a neck 116 in the form of a stem joining a head 117 to the shank 114.

An acetabular component 102 is fixed in the hip bone I.

As previously, an intermediate component 103 is formed by a cup 131 in which is clipped a ring 132 made of plastics material. An elongated opening 133 is made in the ring 132 and extends in the direction of an axis $Y_3$.

In a variant, the ring 132 might be made of metal.

The width $l_{133}$ of the opening 133 is smaller than the largest dimension. $L_{117}$ of the head 117 and greater than the diameter $d_{116}$ of the neck 116 in the form of a stem. The smallest dimension $l_{117}$ of the head 117 is substantially equal to the diameter $d_{116}$, this making it possible to introduce the head 117 in an interior volume $V_{103}$ of the component 103, defined between the cup 131 and the ring 132, by aligning the largest dimension of the head 117 on the axis $Y_3$. By rotating the member 115 through about 90° about axis $X_1$ common to the parts 114 and 116, the head 117 is then retained in the volume $V_{103}$.

$S_2$ denotes the concave surface defined by the component 102. $S'_2$ denotes the outer convex surface of the cup 131. The surfaces $S_2$ and $S'_2$ are globally in the form of portions of a sphere, this making it possible to create an articulation between these two surfaces.

As in the first embodiment, a first convex surface of articulation $S'_1$ is made on the outer surface 135 of the ring, around the opening 133.

A convex surface $S'_1$ is formed on a projecting part 137 of the ring 132 of which 136 and 136' denote the longitudinal edges which are parallel to axis $Y_3$.

A concave surface $S_1$ complementary of the surface $S'_1$ is formed by the metaphyseal part 112 and constitutes the bottom of a depression 119 of globally rectangular section made in the exposed face 112a of the part 112, when the component 101 is in place in the femur F.

The depression 119 is of elongated shape, with its largest dimension located along an axis $Y_1$ globally parallel to axis $Y_3$ when the prosthesis is in mounted configuration. 118 and 118' denote the longitudinal edges of the depression 119. The distance $d_{118}$ between these edges is slightly greater than the width of the part 137 which corresponds, in fact, to the distance $d_{136}$ between the edges 136 and 136'. This contributes to the lateral guiding between the components 101 and 103, as the part 137 is partially engaged in the depression or slideway 119 when the components 1 and 3 are in abutment on each other.

The surfaces $S_1$ and $S'_1$ may be in the form of portions of a sphere or portions of a cylinder with a circular base and rectilinear generatrix.

In the third form of embodiment of the invention, shown in FIGS. 8 to 13, elements similar to those of the first embodiment bear identical references increased by 200. The prosthesis P of this embodiment is intended to fit a patient's shoulder and comprises a humeral component 201 presenting substantially the same geometry as the humeral component of the first embodiment. A member 215 is intended to be anchored by a shank 214 in a housing 213 made in the metaphyseal part 212 of the component 201. The member 215 has substantially the same geometry as the member 15 of the first embodiment except that its head 217 is of globally rectangular section. As in the first embodiment, the member 215 defines a concave surface of articulation $S_1$.

A glenoidal component 202 is intended to be fixed in the glenoid cavity and defines a likewise concave surface $S_2$.

An intermediate component 203, provided to be disposed between the components 201 and 202, is formed by a cup 231 and a ring 232 immobilized on this cup by any appropriate means, for example by crimping. The ring 232 defines an elongated opening 233 for receiving and guiding a stem-shaped neck 216 which joins the head 217 to a flange 218 and to the shank 214, the flange 218 defining the surface $S_1$.

A convex surface $S'_1$ complementary of surface $S_1$ is formed on the outer surface 235 of the ring 232, while the outer surface $S'_2$ of the cup 231 is complementary of the surface $S_2$.

Figure 10:
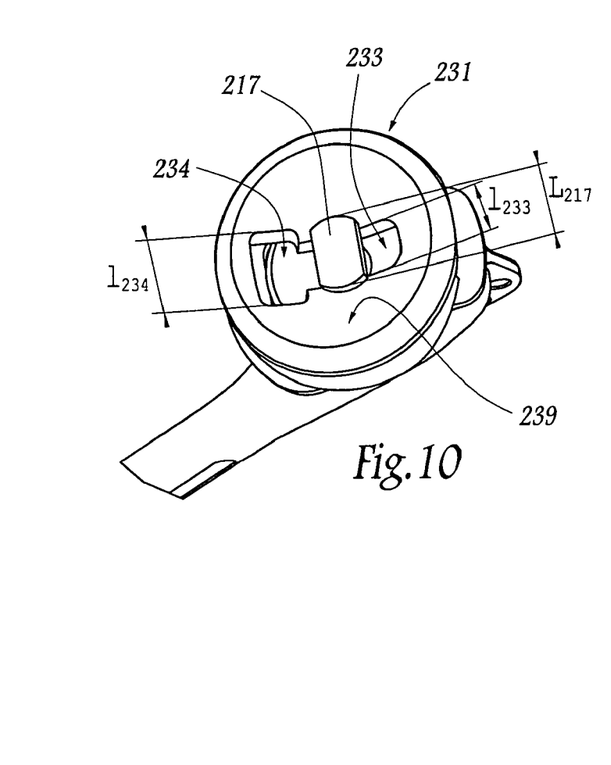
FIG. 10 is a view in perspective of a part of the intermediate component and of the humeral component in the configuration of FIGS. 8 and 9.
Figure 11:
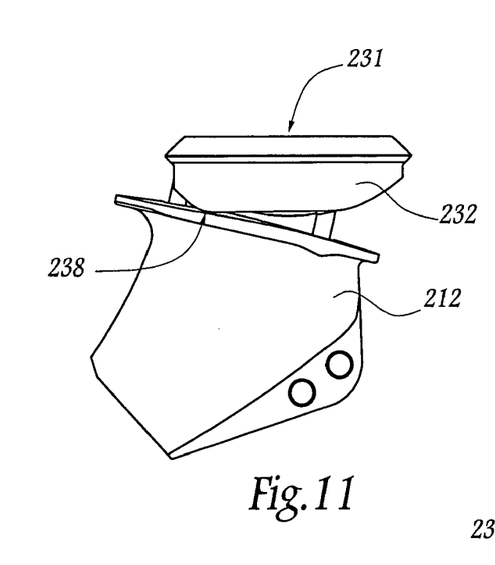
FIG. 11 is a side view of the prosthesis of FIGS. 8 to 10 in another configuration.
Figure 12:
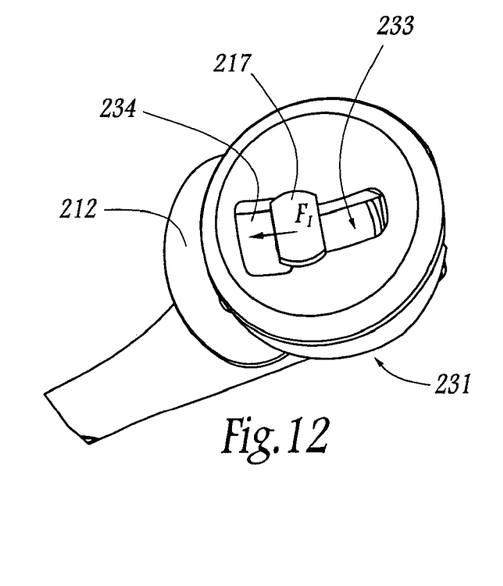
FIG. 12 is a view in perspective similar to FIG. 10, when the prosthesis is in the configuration of FIG. 11.
Figure 13:
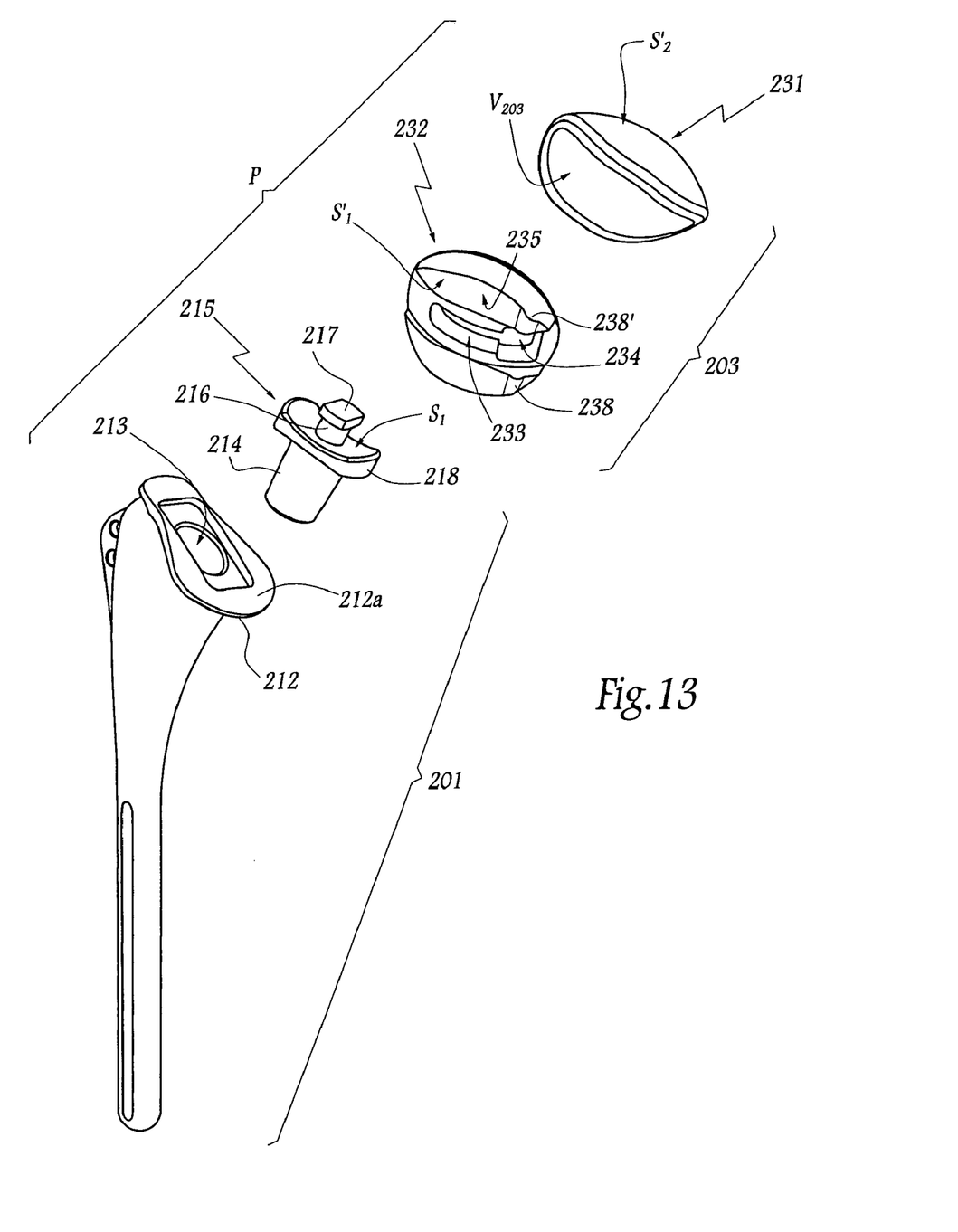
FIG. 13 is an exploded view in perspective of the humeral and intermediate components of the prosthesis of FIGS. 8 to 12.

As is more particularly visible in FIGS. 10 and 12 where the cup 231 has been omitted to render the drawings clearer, the head 217 has a length $L_{217}$ greater than the width $l_{233}$ of the opening 233 over the greatest part of its length. In order to allow the introduction of the head 217 in the interior volume $V_{203}$ of the component 203, the opening 233 is provided with a widened zone 234 made in the vicinity of one of its ends and of which the width $l_{234}$ is greater than the length $L_{217}$. In order to guarantee that the head 217 is retained in the volume $V_{203}$, the ring 232 is provided with two heels 238 and 238' intended to come into abutment against the exposed face 212a of the metaphyseal part 212 when the component 201 is in place in the humerus, this blocking the ring 232 in the configuration of FIGS. 11 and 12 and avoiding a displacement of the head 217 in the direction of arrow $F_1$ in FIG. 12, thus preventing an alignment of this head with the opening 204 and, consequently, the withdrawal of the head 217 from the volume $V_{203}$. In this way, when the head 217 has been introduced in the volume 11203, it participates in the resistance of the assembly of the prosthesis P.

According to a variant of the invention (not shown), the function of the heels 238 and 238' might be performed by one or more elements in relief made on the inner surface 239 of the ring 232, for example on either side of the opening 233 and in the vicinity of the zone 234. The one or more elements in relief would in that case prevent the head 217 from moving towards the left from its position in FIG. 12.

According to another variant of the invention (not shown), elements in relief with the same function as the heels 238 and 238' may be provided on the face 212a, and even on both components 201 and 203.

The width $l_{233}$ is slightly greater than the diameter $d_{216}$ of the stem 216.

As in the first embodiment, the surface $S'_1$ is defined between the edges parallel to direction $Y_3$ forming a slideway and between which the flange 218 may be introduced. Similarly, the surfaces $S_1$ and $S'_1$ may be portions of a sphere or of a cylinder, and even of other surfaces of adapted shape.

The invention has been shown when used in total shoulder and hip prostheses. However, it is applicable with a shoulder prosthesis not having a glenoidal component, the anatomical surface of articulation of the glenoid cavity being used instead of the surface $S_2$ represented in the Figures. Similarly, in the case of a hip prosthesis, the natural acetabular cavity may be used.

The characteristics of the different forms of embodiment may be combined together. In particular, the prosthesis of the second embodiment may be adapted to the shoulder, while the prostheses of the first and third embodiments may be adapted to the hip.

What is claimed is:

1. Shoulder or hip prosthesis comprising a first component, humeral or femoral, presenting a concave surface of articulation and a second, intermediate component presenting first and second convex surfaces of articulation intended to cooperate respectively with the concave surface of articulation of the first component and with a glenoidal or acetabular concave surface of articulation which is natural or defined by a third, glenoidal or acetabular component, the second component being hollow and defining a volume for receiving a part of a member belonging to the first component, the part being connected to a metaphyseal part of the first component by a stem traversing an opening made in a ring of the second component, mounted on a cup of which the outer surface forms the second convex surface of articulation of the second component, wherein the first convex surface of articulation of the second component is formed on the outer surface of the ring, around the opening and wherein the second convex surface of articulation of the second component is unconstrained relative to the concave surface of articulation of the third component.

2. The prosthesis of claim 1, wherein the opening is elongated with a width less than a maximum width of the part of the member received in the volume, the width of the opening being slightly greater than a width of the stem.

3. The prosthesis of claim 1, wherein the concave surface of articulation of the first component is formed on a portion of the member which is in one piece with the part and the stem, the member being added on the metaphyseal part of the first component.

4. The prosthesis of claim 1, wherein the concave surface of articulation of the first component is formed on the metaphyseal part of the first component.

5. The prosthesis of claim 1, wherein one of the surfaces, from the first convex surface of the second component and the concave surface of the first component, projects with respect to the component to which it belongs, while the other of the surfaces, from the same two surfaces, is recessed with respect to the other component, the projecting surface being bordered by two globally parallel edges, while the recessed surface is bordered by two globally parallel edges between which the edges of the projecting surface are disposed when the prosthesis is in a mounted configuration.

6. The prosthesis of claim 1, wherein the second component comprises a hollow slideway for receiving and guiding a projecting part of the first component, the first convex surface of articulation of the second component being formed by a bottom of the slideway and the concave surface of articulation of the second component being formed by an end surface of the projecting part.

7. The prosthesis of claim 1, wherein the opening is provided with a widened zone of introduction for the part of the member in the receiving volume.

8. The prosthesis of claim 7, wherein the ring is elastically deformable at least at the level of the widened zone, so as to allow the introduction of the part in the volume.

9. The prosthesis of claim 7, wherein the widened zone is made at one end of the opening which is elongated, at least one of the first and second components being provided with at least one element in relief for blocking, adapted to prevent alignment of the part and the widened zone when the prosthesis is in a mounted configuration.

10. The prosthesis of claim 1, wherein the first convex surface of articulation is globally in a form of a truncated cylinder centred on an antero-posterior axis of a joint when the prosthesis is in a mounted and implanted configuration.

11. A shoulder or hip prosthesis comprising:
a first component comprising:
a metaphyseal part;
a concave surface of articulation; and
a member having a head and a stem, wherein the stem connects the member to the metaphyseal part;
a second, intermediate component comprising:
a ring having an opening and an outer surface, wherein the outer surface of the ring defines a first convex surface of articulation; and
a cup having an outer surface, wherein the outer surface of the cup defines a second convex surface of articulation;
wherein the ring is mounted to the cup;
wherein the second component is hollow and defines a volume for receiving the head of the member of the first component;
and wherein the head is connected to the second component by traversing the opening in the ring; and a third component having a concave surface of articulation;
wherein the first convex surface of articulation of the second component is adapted to cooperate with the concave surface of articulation of the first component and the second convex surface of articulation of the second component is adapted to cooperate with the concave surface of articulation of the third component; and
wherein the second convex surface of articulation of the second component is unconstrained relative to the concave surface of articulation of the third component.

12. The prosthesis of claim 11, wherein the opening of the ring is elongated and has a width less than a maximum width of the head and greater than a width of the stem.

13. The prosthesis of claim 11, wherein the concave surface of articulation of the first component is formed by a flange positioned between the stem and the head of the member.

14. The prosthesis of claim 11, wherein the first convex surface of articulation of the second component has a projecting surface and the concave surface of articulation of the first component has a recessed surface, and wherein the projecting surface is bordered by a first pair of parallel edges and the recessed surface is bordered by a second pair of parallel edges.

15. The prosthesis of claim 14, wherein the first pair of parallel edges are disposed between the second pair of parallel edges when the prosthesis is in a mounted configuration.

16. The prosthesis of claim 11, wherein the second component comprises a hollow slideway for receiving and guiding a projecting part of the first component, and wherein the first convex surface of articulation of the second component is formed by a bottom of the slideway and the concave surface of articulation of the first component is formed by an end surface of the projecting part.

17. The prosthesis of claim 11, wherein the opening of the ring has a widened zone for introducing the head of the member into the volume.

18. The prosthesis of claim 17, wherein the widened zone of the opening of the ring is elastically deformable to allow introduction of the head into the volume.

19. The prosthesis of claim 17, wherein the opening is elongated and the widened zone is formed at one end of the opening, and wherein at least one of the first and second components has an element adapted to prevent alignment of the head and the widened zone when the prosthesis is in a mounted configuration.

20. The prosthesis of claim 19, wherein the element is a relief element.

21. The prosthesis of claim 11, wherein the first convex surface of articulation of the second component is in a form of a truncated cylinder centered on an antero-posterior axis of a joint when the prosthesis is in a mounted and implanted configuration.

22. A shoulder or hip prosthesis comprising:
a first member comprising a head connected to a metaphyseal part by a stem;
an intermediate component comprising a first articulation surface on an outer surface of a ring and a second articulation surface on an outer surface of a cup, the first articulation surface comprising an opening to a volume within the intermediate component that receives the head of the first member and connects the first member to the intermediate component such that the first articulation surface articulates with respect to an articulation surface defined by a flange of the first member as the stem moves within the opening; and a second member comprising an articulation surface that articulates with respect to the second articulation surface of the intermediate member;

wherein the second articulation surface of the intermediate component is unconstrained relative to the articulation surface of the second member.

23. The prosthesis of claim 22, wherein the articulation surface of the first member is concave and the first articulation surface of the intermediate component is convex.

24. The prosthesis of claim 22, wherein the articulation surface of the second member is concave and the second articulation surface of the intermediate component is convex.

25. The prosthesis of claim 22, wherein the opening is elongated and has a width less than a maximum width of the head and greater than a width of the stem.

26. A shoulder or hip prosthesis comprising:
   a first component comprising:
      a head portion; and
      a flange connected to the head portion, wherein the flange defines a concave surface of articulation;
   a second, intermediate component comprising:
      a ring defining a first convex surface of articulation;
      a cup defining a second convex surface of articulation;
      wherein the ring and the cup define a volume for receiving the head portion of the first component;
      and wherein the head portion is introduced in the volume by traversing an opening in the ring; and
   a third component having a concave surface of articulation;
   wherein the first convex surface of articulation of the second component is adapted to cooperate with the concave surface of articulation of the first component and the second convex surface of articulation of the second component is adapted to cooperate with the concave surface of articulation of the third component;
   wherein the second convex surface of articulation of the second component is unconstrained relative to the concave surface of articulation of the third component.

\* \* \* \* \*

UNITED STATES PATENT AND TRADEMARK OFFICE
CERTIFICATE OF CORRECTION

PATENT NO. : 7,470,287 B2
APPLICATION NO. : 11/165287
DATED : December 30, 2008
INVENTOR(S) : Alain Tornier et al.

It is certified that error appears in the above-identified patent and that said Letters Patent is hereby corrected as shown below:

On Page 2, Title Page: item (56);

Under U.S. Patent Documents:

Remove "4,693,372" and replace it with -- 4,693,723 --

On Page 3, Title Page: item (56);

Remove "2005/0256684" and replace it with -- 2005/0256584 --

Column 6, line 17

Remove "11203" and replace it with -- $V_{203}$ --

Signed and Sealed this

Sixteenth Day of June, 2009

JOHN DOLL
*Acting Director of the United States Patent and Trademark Office*